(12) United States Patent
Zhang

(10) Patent No.: US 12,257,412 B2
(45) Date of Patent: Mar. 25, 2025

(54) WIRELESS TATTOO DEVICE

(71) Applicant: INK PROJECTS LLC, Fort Mill, SC (US)

(72) Inventor: Shujie Zhang, Jinhua (CN)

(73) Assignee: INK PROJECTS LLC, Fort Mill, SC (US)

( * ) Notice: Subject to any disclaimer, the term of this patent is extended or adjusted under 35 U.S.C. 154(b) by 486 days.

(21) Appl. No.: 17/320,745

(22) Filed: May 14, 2021

(65) Prior Publication Data

US 2021/0353924 A1    Nov. 18, 2021

Related U.S. Application Data

(60) Provisional application No. 63/024,881, filed on May 14, 2020.

(51) Int. Cl.
*A61M 37/00* (2006.01)

(52) U.S. Cl.
CPC ..... *A61M 37/0076* (2013.01); *A61M 2205/10* (2013.01); *A61M 2205/502* (2013.01); *A61M 2205/586* (2013.01); *A61M 2205/8206* (2013.01)

(58) Field of Classification Search
CPC .......... A61M 37/0076; A61M 2205/10; A61M 2205/586
See application file for complete search history.

(56) References Cited

U.S. PATENT DOCUMENTS

| | | |
|---|---|---|
| D422,359 S | 4/2000 | Fitch |
| 6,345,553 B1 | 2/2002 | Adler |
| 6,505,530 B2 | 1/2003 | Adler |
| 10,471,246 B1 | 11/2019 | Lipscomb |
| 10,493,255 B2 | 12/2019 | Fok |
| D909,576 S | 2/2021 | Wang |
| D910,846 S | 2/2021 | Siciliano |
| D912,818 S | 3/2021 | Siciliano |
| 10,960,193 B1 * | 3/2021 | Reeves ............. A61M 37/0076 |
| D927,951 S | 8/2021 | Haringer |
| D940,306 S | 1/2022 | Osypka |
| D940,307 S | 1/2022 | Osypka |
| 12,011,564 B2 | 6/2024 | Xiao |
| D1,034,995 S | 7/2024 | Aguiar et al. |
| D1,034,996 S | 7/2024 | Aguiar et al. |

(Continued)

OTHER PUBLICATIONS http://www.dragonhawktattoosupply.com/dragonhawk-essence-pen-style-rotary-tattoo-machine-rca-cord-2pcs-nonwovens-grip-cover-self-adhesive-machine.html [Dated Aug. 31, 2019] (Year: 2019).*

(Continued)

*Primary Examiner* — Erin McGrath
(74) *Attorney, Agent, or Firm* — Volpe Koenig

(57) ABSTRACT

A wireless tattoo device is disclosed. The device includes an electronics housing, a control panel, a power source, and a motor assembly driven by the power source. A motor housing is attached to the electronics housing, and the motor housing defines a passage dimensioned to receive a portion of the motor assembly. A grip defines an opening dimensioned to receive an end of the motor housing. The motor housing is configured to receive a needle cartridge. The motor housing and the grip are rotatable relative to each other such that a depth of the needle cartridge relative to the grip varies based on a relative rotation position between the motor housing and the grip.

16 Claims, 14 Drawing Sheets

(56) References Cited

U.S. PATENT DOCUMENTS

| | | | |
|---|---|---|---|
| 2007/0203504 A1 | | 8/2007 | Denny et al. |
| 2008/0300615 A1* | | 12/2008 | Colton ............... A61M 37/0076 |
| | | | 606/186 |
| 2009/0090218 A1 | | 4/2009 | Jarboe et al. |
| 2016/0074646 A1 | | 3/2016 | Norman |
| 2016/0121093 A1* | | 5/2016 | Fan ......................... H04W 4/80 |
| | | | 606/185 |
| 2018/0043146 A1* | | 2/2018 | Vescovi ............ A61M 37/0076 |
| 2018/0110926 A1 | | 4/2018 | Schrul |
| 2018/0369553 A1* | | 12/2018 | Siciliano ............ A61B 17/3476 |
| 2019/0022366 A1 | | 1/2019 | Fok |
| 2019/0133299 A1 | | 5/2019 | Marchesano |
| 2020/0016389 A1* | | 1/2020 | Wehinger .......... A61M 37/0076 |
| 2020/0114137 A1 | | 4/2020 | Siciliano |
| 2021/0244928 A1 | | 8/2021 | Siciliano |
| 2021/0322747 A1 | | 10/2021 | Grassano |
| 2021/0353924 A1 | | 11/2021 | Zhang |
| 2021/0393937 A1 | | 12/2021 | Siciliano |

OTHER PUBLICATIONS

Ambition Soldier Rotary Battery Pen Tattoo Cartridge Machine, first available Jul. 16, 2022, amazon.com, [online], site visited Jan. 3, 2024], Available from internet URL: https://www.amazon.com. Ambition-Cartridge-Wireless-Coreless-Equipment/dp/B0BC1BC957/ (Year: 2022).

EZ Tattoo Kit, first available Sep. 12, 2022, amazon.com, [online], site visited Jan. 3, 2024], Available from internet URL: https://www.amazon.com/EZ-Tattoo-Kit-Cartridge-Beginners/dp/B0CM673976/ (Year: 2022).

Wireless Rotary Pen Machine, amazon.com, [online], [site visited Jan. 3, 2024], Available from internet URL: https://www.amazon.com/Wireless-Machine-Beoncall-Cartridge-Tattooing/dp/B08CC1WQ24 (Year:2024).

Yuelong Rotary Tattoo Machine Kit, first available Jan. 16, 2021, amazon.com, [online], site visited Jan. 3, 2024], Available from internet URL: https://www.amazon.com/Wireless-Kit-Yuelong-Cartridge-Cartridges-Permanent/dp/B08GXC9T4S (Year: 2021).

Professional Wireless Tattoo Pen Machine, redtoptattoo.com, [online], site visited Jan. 3, 2024], Available from internet URL: https://www.redtoptattoo.com/tattoo-machine/tattoo-pens/spark-brand-tattoo-cartridge-machine-wireless.html (Year: 2024).

Dragonhawk Mast Saber, first available Dec. 23, 2023, aliexpress.US [online], [site visited Jan. 3, 2024], Available from internet URL: https://www.dragonhawktattoos.com/collections/tattoo-machines/products/dragonhawk-mast-saber-wireless-battery-rotary-tattoo-machine-pen (Year: 2020).

Professional Wireless Battery Pen, first available Dec. 23, 2023, aliexpress.us [online], [site visited Jan. 3, 2024], Available from internet URL: https://www.aliexpress.US/item/3256806001031804.html?gatewayAdapt=glo2usa4itemAdapt (Year: 2023).

Wireless Rotary Tattoo Machine, first available Jun. 14, 2020, dhgate.com, [online], [site visited Jan. 3, 2023], Available from internet URL: https://www.dhgate.com/product/wireless-rotary-tattoo-machine/lcd-display/520753165.html (Year: 2020).

Wireless Tattoo Pen Multi-handle Motor Tattoo All-in-one EM158, hawink.com, [online], [site visited Jan. 3, 2024], Available from internet URL: https://hawink.com/products/wireless-tattoo-pen-multi-handle-motor-tattoo-all-in-one-gray-charged-em158 (Year: 2024).

Kings tattoo supply Trillium wireless pen, first available Jan. 3, 2020, instagram.com, [online], [site visited Oct. 25, 2024], Available from internet URL: https://instagram.com/p/B62nzTJIOBo/?img_index=1 (Year: 2020).

* cited by examiner

WIRELESS TATTOO DEVICE

CROSS-REFERENCE TO RELATED APPLICATION

This application claims priority to U.S. Provisional Patent Application No.: 63/024,881, filed May 14, 2020, the disclosure of which is hereby incorporated by reference as if set forth in its entirety herein.

FIELD OF INVENTION

The present disclosure relates to a wireless tattoo pen.

BACKGROUND

Tattoo devices, commonly referred to as tattoo pens, are well known. Tattoo pens typically require a power supply via a wired connection in order to operate the pen. It can be difficult to maneuver the tattoo device based on the wired power connection. The wired power connection can obstruct a tattoo artist's view or otherwise make it more difficult for a tattoo artist to draw a particular design on a customer. This results in an increase in the amount of time required to complete a tattoo and also makes it more difficult to sketch intricate details in a particular tattoo design.

It would be desirable to provide a tattoo device that does not require a wired power connection that is more convenient and easier to use than existing tattoo devices.

SUMMARY

A wireless tattoo device is disclosed. The device includes an electronics housing, a control panel, a power source, and a motor assembly driven by the power source. A motor housing is attached to the electronics housing, and the motor housing defines a passage dimensioned to receive a portion of the motor assembly. A grip defines an opening dimensioned to receive an end of the motor housing. The motor housing is configured to receive a needle cartridge. The motor housing and the grip are rotatable relative to each other such that a depth of the needle cartridge relative to the grip varies based on a relative rotation position between the motor housing and the grip.

In an aspect, the electronics housing includes a power inlet. The power inlet is preferably defined on an axial end cap of the device. The control panel includes an increase button, a decrease button, a power button, and a display. The control panel can also include a voltage indicator, a power indicator, and a time indicator.

The electronics housing includes an outer wall defining a window, and the window is dimensioned to receive the control panel. A first end of the electronics housing is configured to engage with an end cap, and a second end of the electronics housing includes a first mating feature configured to matingly engage with a second mating feature defined on an end of the motor housing.

A first axial height (X1) of the electronics housing is less than a second axial height (X2) of the motor housing. A first radial width (Y1) of the electronics housing is equal to or less than a second radial width (Y2) of the motor housing. The motor assembly is partially housed in both the electronics housing and the motor housing.

In another aspect, the device also includes a needle depth adjustment system which is configured to vary a length of needle extending from a terminal end of the device.

Additional embodiments are disclosed herein.

BRIEF DESCRIPTION OF THE DRAWINGS

The foregoing Summary and the following Detailed Description will be better understood when read in conjunction with the appended drawings, which illustrate a preferred embodiment of the disclosure. In the drawings.

DETAILED DESCRIPTION OF THE PREFERRED EMBODIMENTS

Figure 1:
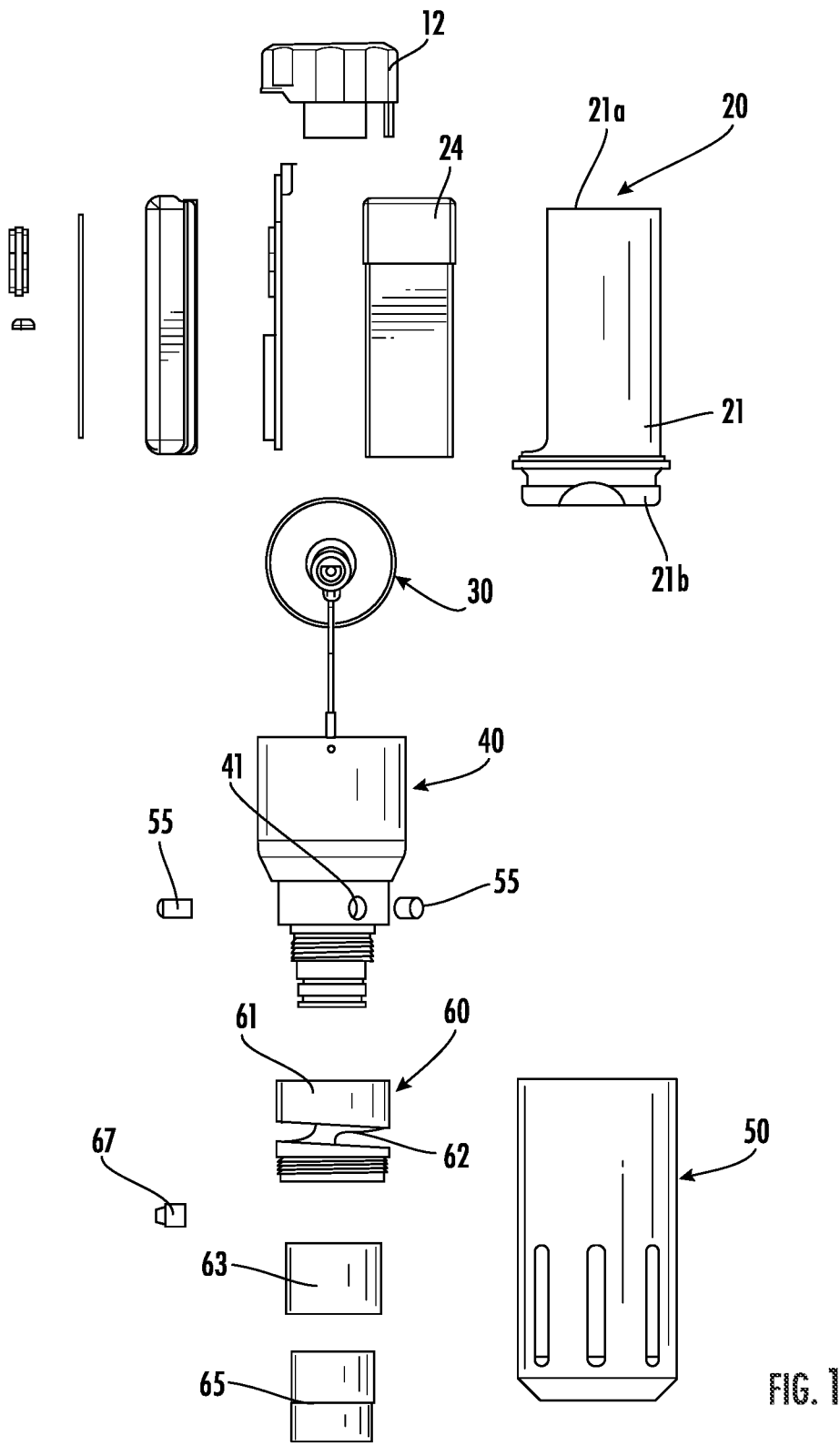
FIG. 1 is an exploded side view of a wireless tattoo device.

Certain terminology is used in the following description for convenience only and is not limiting. The words "front," "rear," "upper" and "lower" designate directions in the drawings to which reference is made. The words "inwardly" and "outwardly" refer to directions toward and away from the parts referenced in the drawings. "Axially" refers to a direction along the axis of a shaft. A reference to a list of items that are cited as "at least one of a, b, or c" (where a, b, and c represent the items being listed) means any single one of the items a, b, or c, or combinations thereof. The terminology includes the words specifically noted above, derivatives thereof and words of similar import.

Figure 2:
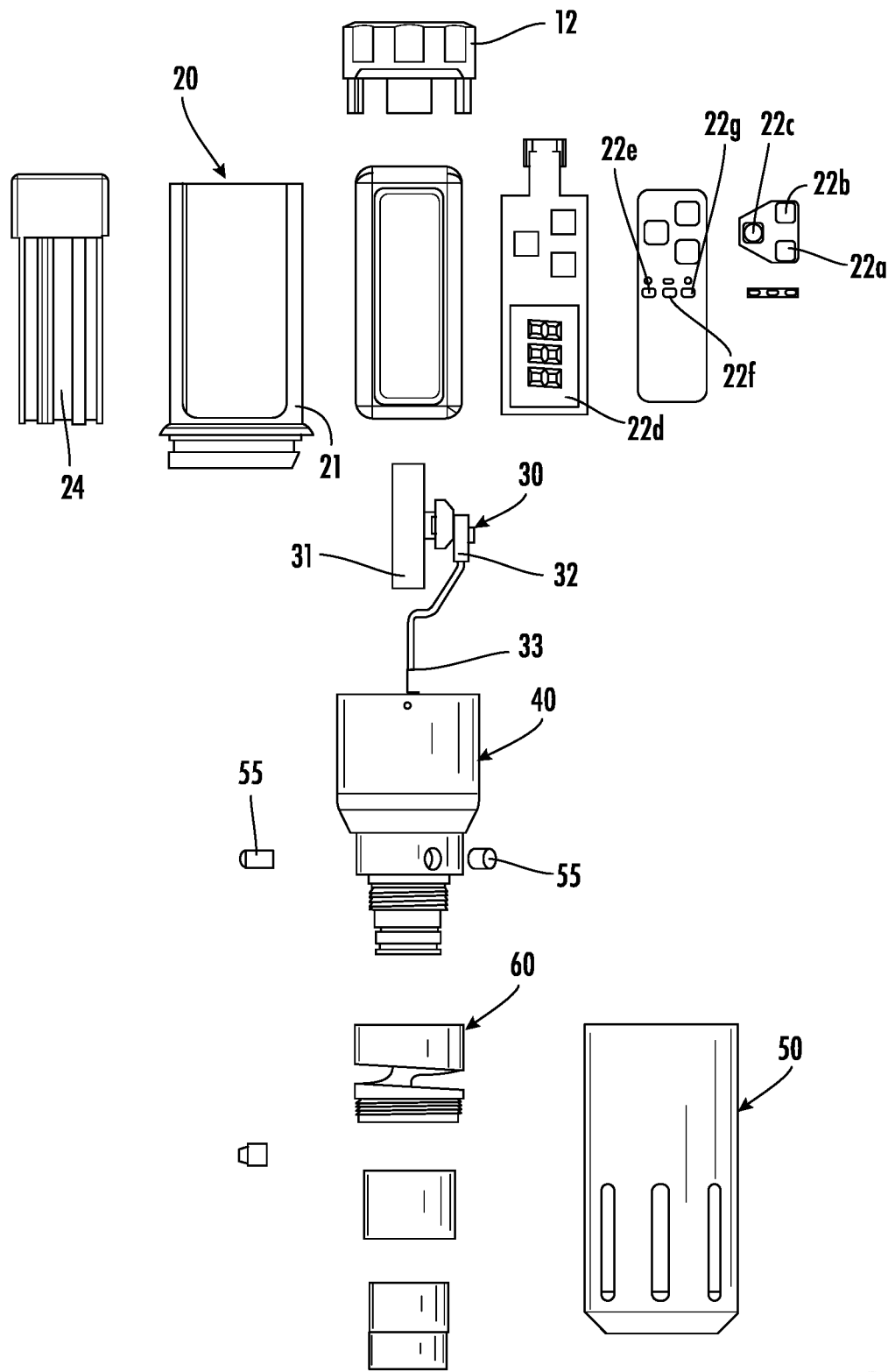
FIG. 2 is an exploded front view of the wireless tattoo device of FIG. 1.
Figure 3:
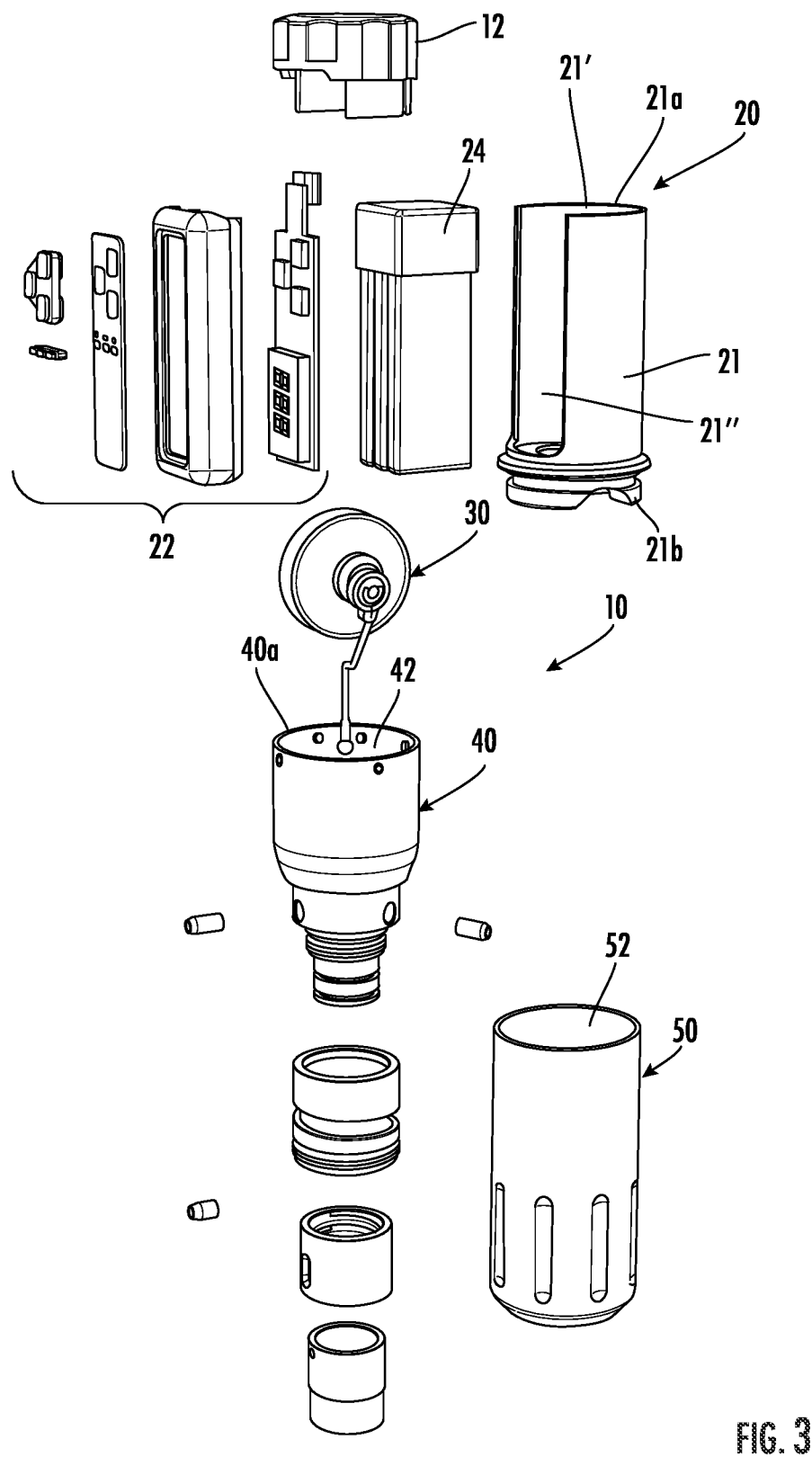
FIG. 3 is a perspective exploded view of the wireless tattoo device of FIGS. 1 and 2.
Figure 4:
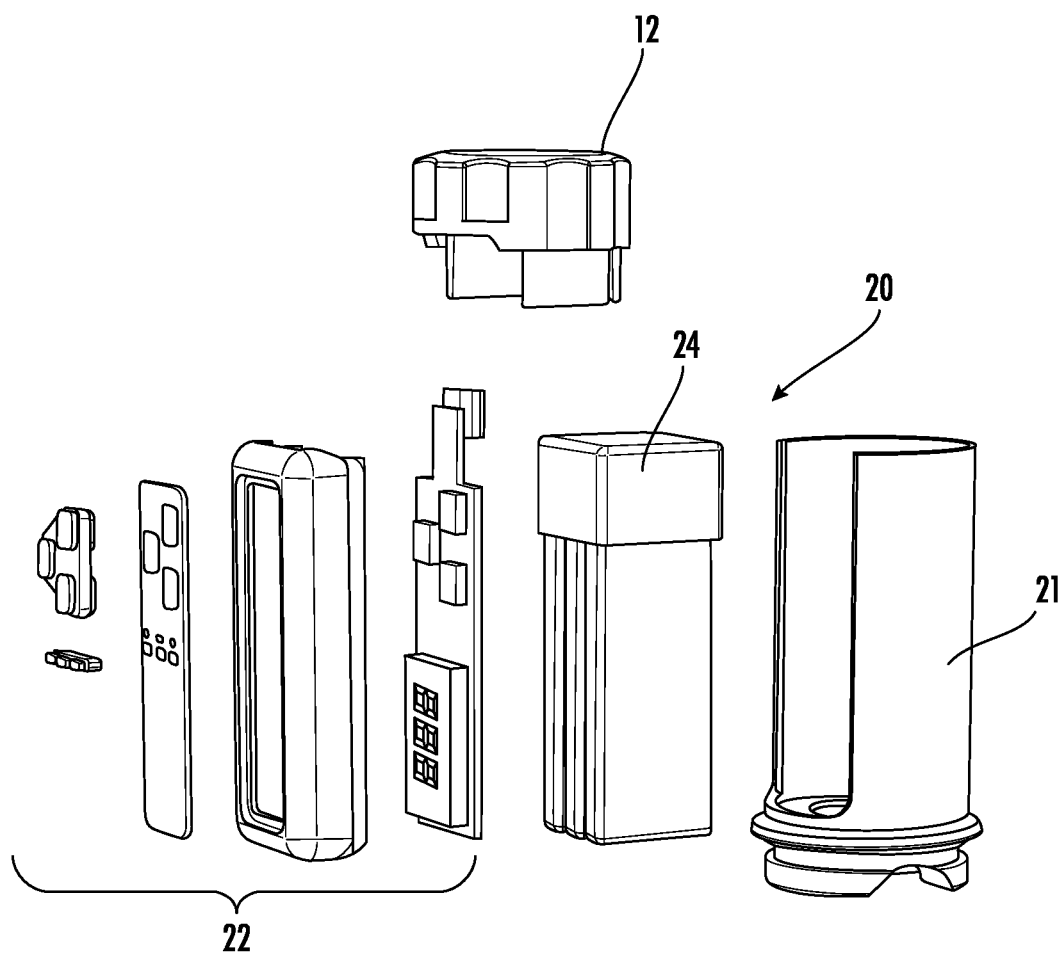
FIG. 4 is a perspective exploded view of an electronics assembly of the wireless tattoo device of FIGS. 1-3.

As generally shown in FIGS. 1-3, a wireless tattoo device 10 is disclosed herein. The device 10 includes an electronics assembly 20 including an electronics housing 21, shown in FIG. 4. Inside of the electronics housing 21, the electronics assembly 20 includes a control panel 22, a power source 24, and a motor assembly 30 driven by the power source 24. The device 10 is completely wireless. In one embodiment, the power source 24 is a rechargeable battery.

Figure 9:
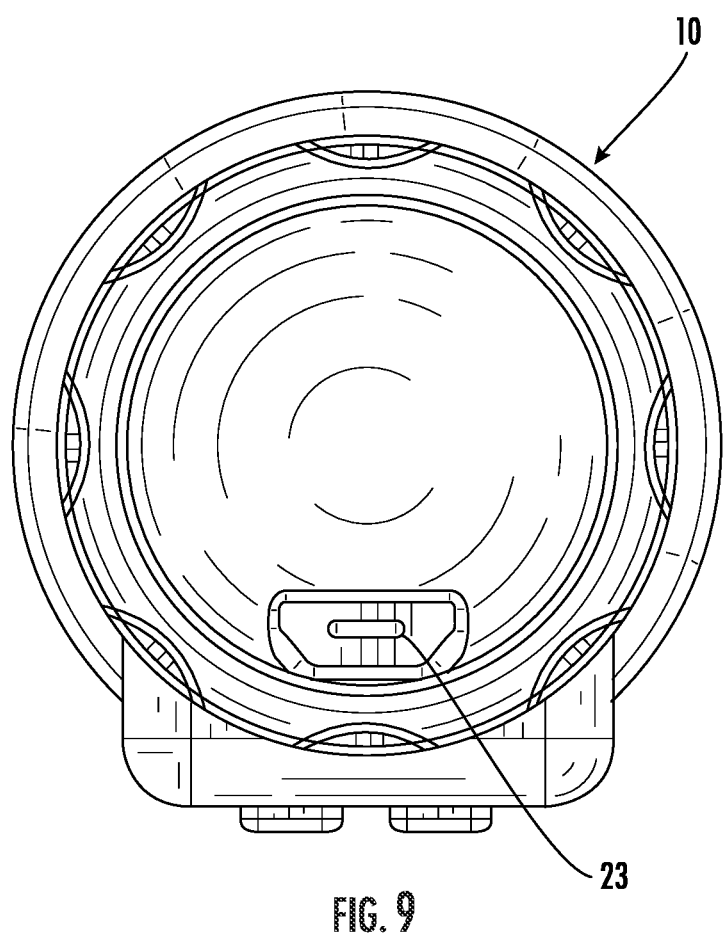
FIG. 9 is a top view of the wireless tattoo device.
Figure 11:
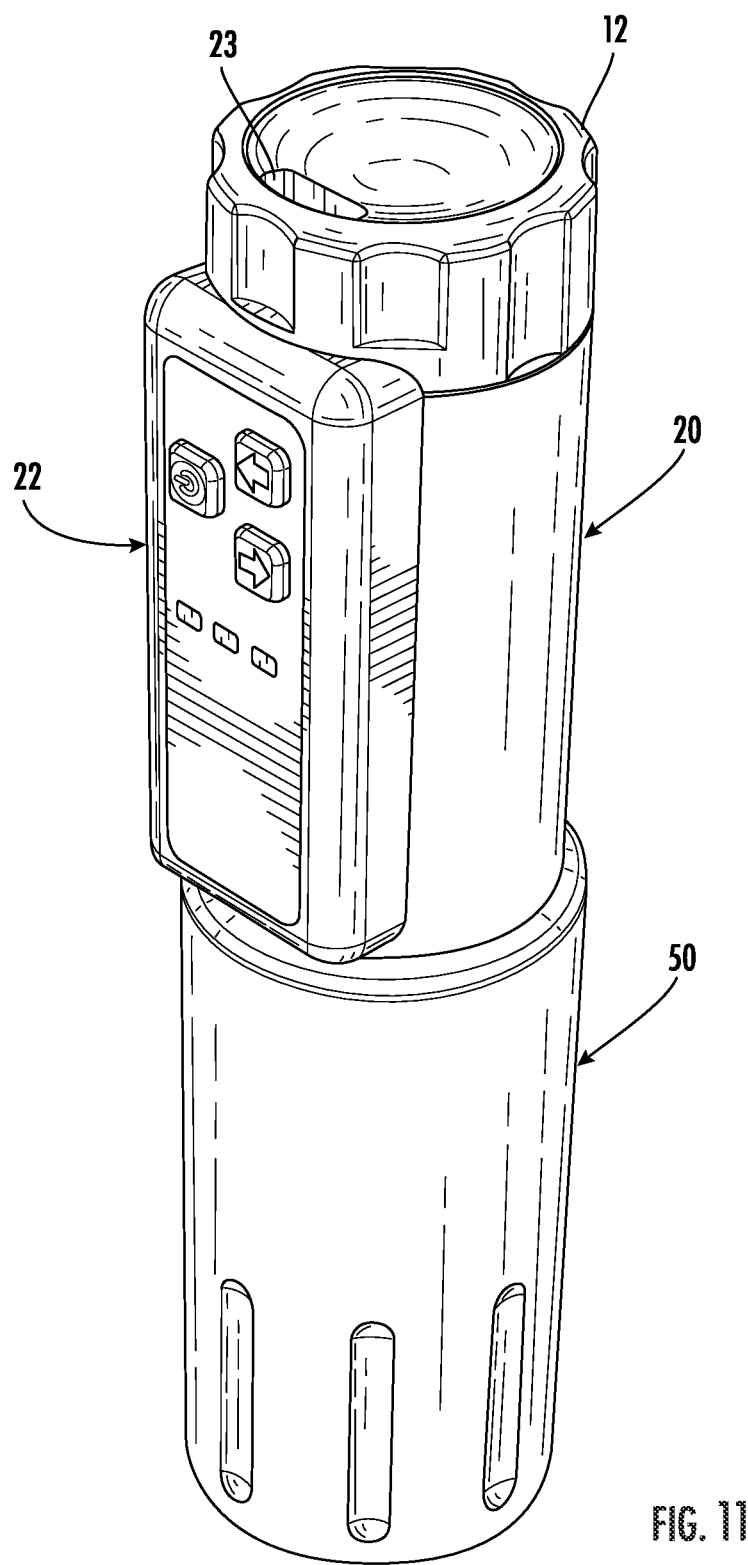
FIG. 11 is a perspective view of the wireless tattoo device in an assembled state.

In one embodiment, the electronics assembly 20 includes a power inlet 23. The power inlet 23 can be a micro USB connection (as shown in FIGS. 9 and 11). In other embodiments, the power inlet 23 includes a standard USB connection. In one embodiment, the power inlet 23 is defined on an axial end cap 12 of the device 10. One of ordinary skill in the art would recognize that the power inlet can include other types of configurations within the scope of this application.

In one embodiment, the electronics housing 21 includes an outer wall 21' defining a window 21", and the window 21" is dimensioned to receive the control panel 22.

Figure 6:
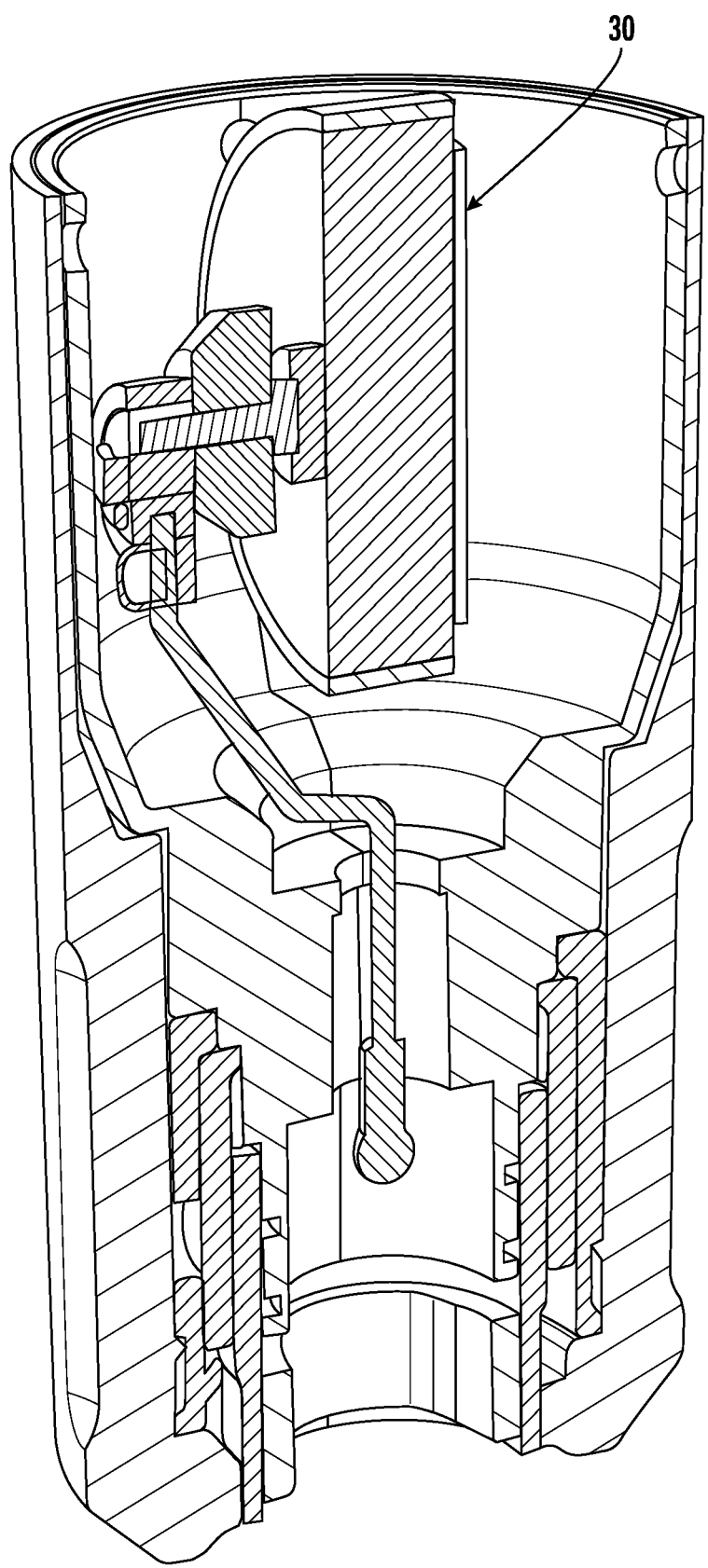
FIG. 6 is a perspective cross-sectional view of a motor assembly of the wireless tattoo device of FIGS. 1-3.
Figure 7:
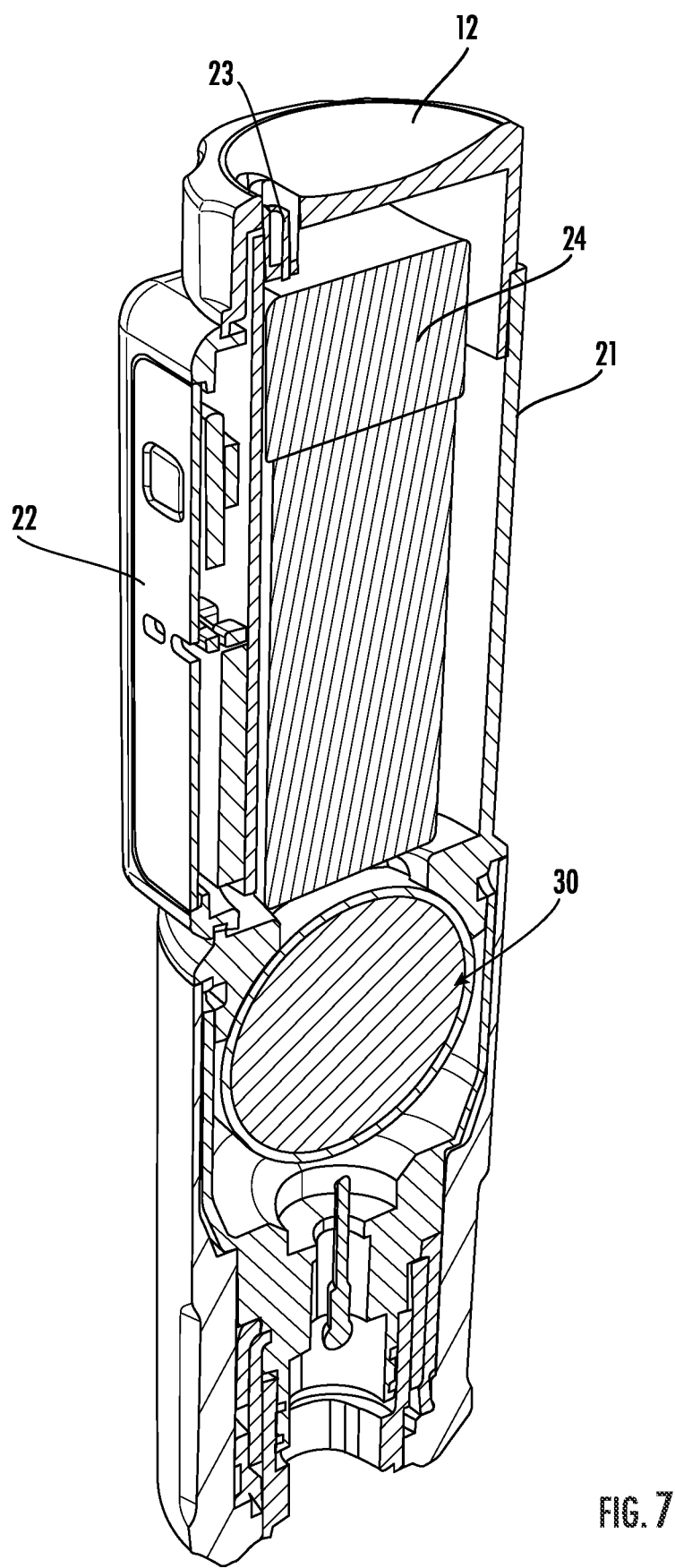
FIG. 7 is a perspective cross-sectional view of the motor assembly and electronics assembly of the wireless tattoo device of FIGS. 1-3.
Figure 8:
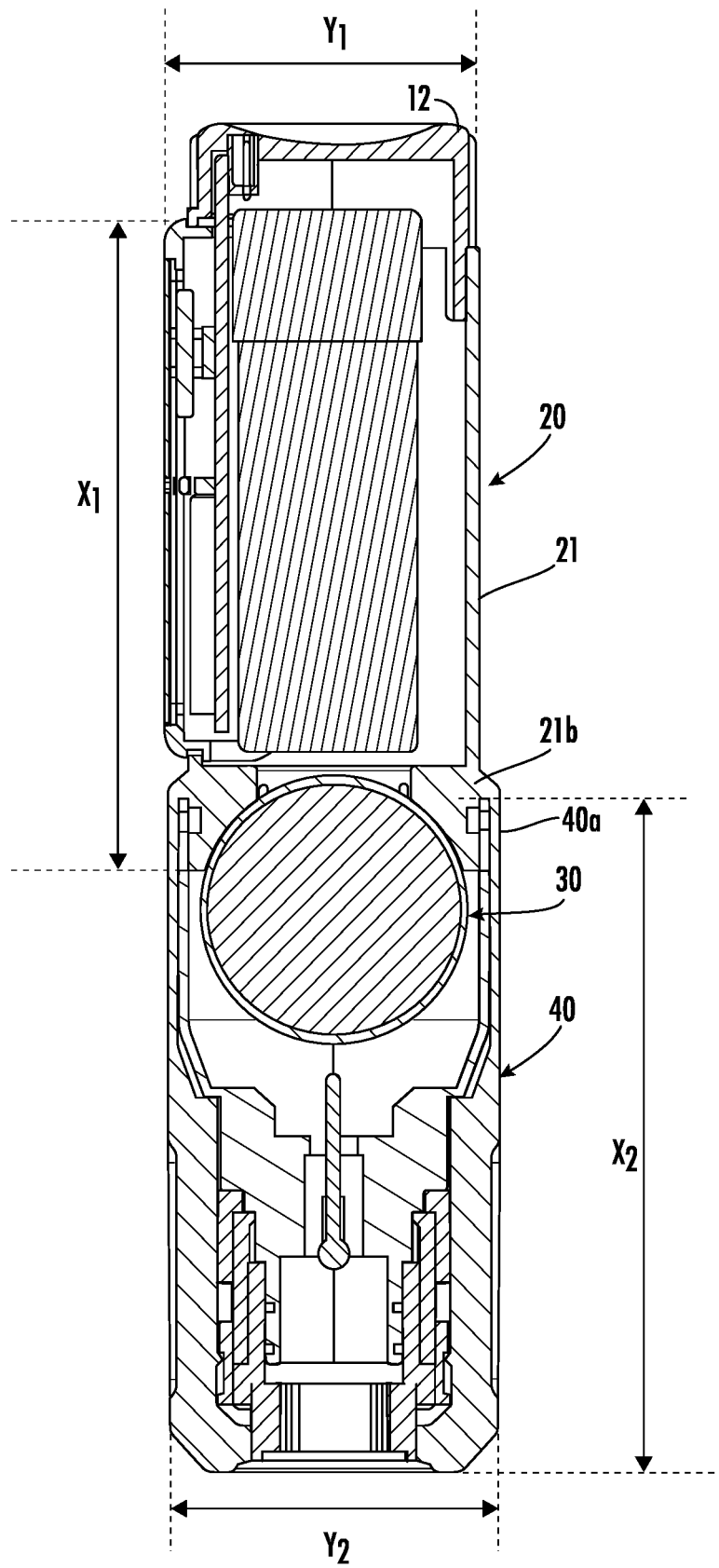
FIG. 8 is a side cross-sectional view of the electronics assembly, motor assembly, and the motor housing of the wireless tattoo device of FIGS. 1-3.

The motor assembly 30, shown in detail in FIGS. 6-8, can preferably include a DC motor. However, one of skill in the art will recognize that other types of motors can be utilized without departing from the scope of the present disclosure. In one embodiment, the device 10 has a continuous operation mode for the motor assembly 30. The motor assembly 30 can include a master wheel 31, a stroke wheel 32, and a striker or actuator 33. The master wheel 31 rotationally engages the stroke wheel 32 which drives the striker or actuator 33.

A motor housing 40 is provided that is attached to the electronics housing 21. The motor housing 40 defines a passage 42 dimensioned to receive a portion of the motor assembly 30. The motor housing 40 is configured to receive a needle cartridge, including a needle 64. The motor housing 40 can also include a gear feedback system.

A grip 50 defines an opening 52 dimensioned to receive an end of the motor housing 40. The motor housing 40 and the grip 50 are rotatable relative to each other such that a depth of the needle cartridge relative to the grip 50 varies based on a relative rotation position between the motor housing 40 and the grip 50.

As shown in FIG. 8, a first axial height (M) of the electronics housing 21 is less than a second axial height (X2) of the motor housing 40. This configuration provides a more compact device 10 for a user that is easily maneuverable.

As shown in FIG. 8, the electronics housing 21 and the motor housing 40 have a nearly identical radial width. In one embodiment, a first radial width (Y1) of the electronics housing 21 is equal to or less than a second radial width (Y2) of the motor housing 40. As used herein, the radial width of the electronics housing 21 and the motor housing 40 are within 5% of each other.

In one embodiment, the device 10 has an overall axial height of 131 mm, +/−10 mm. The device 10 preferably has an outermost diameter of 32 mm, +/−5 mm with the grip attached.

A first end 21a of the electronics housing 21 is preferably configured to engage with the end cap 12, and a second end 21b of the electronics housing 21 preferably includes a first mating feature configured to matingly engage with a second mating feature defined on an end 40a of the motor housing 40. The mating features can include a groove, hole, opening, threads, or other feature configured to allow a connection or joining the electronics housing 21 with the motor housing 40. In one embodiment, fastening elements, such as a bolt or screw, can be provided to secure the electronics housing 21 to the motor housing 40.

Figure 14:
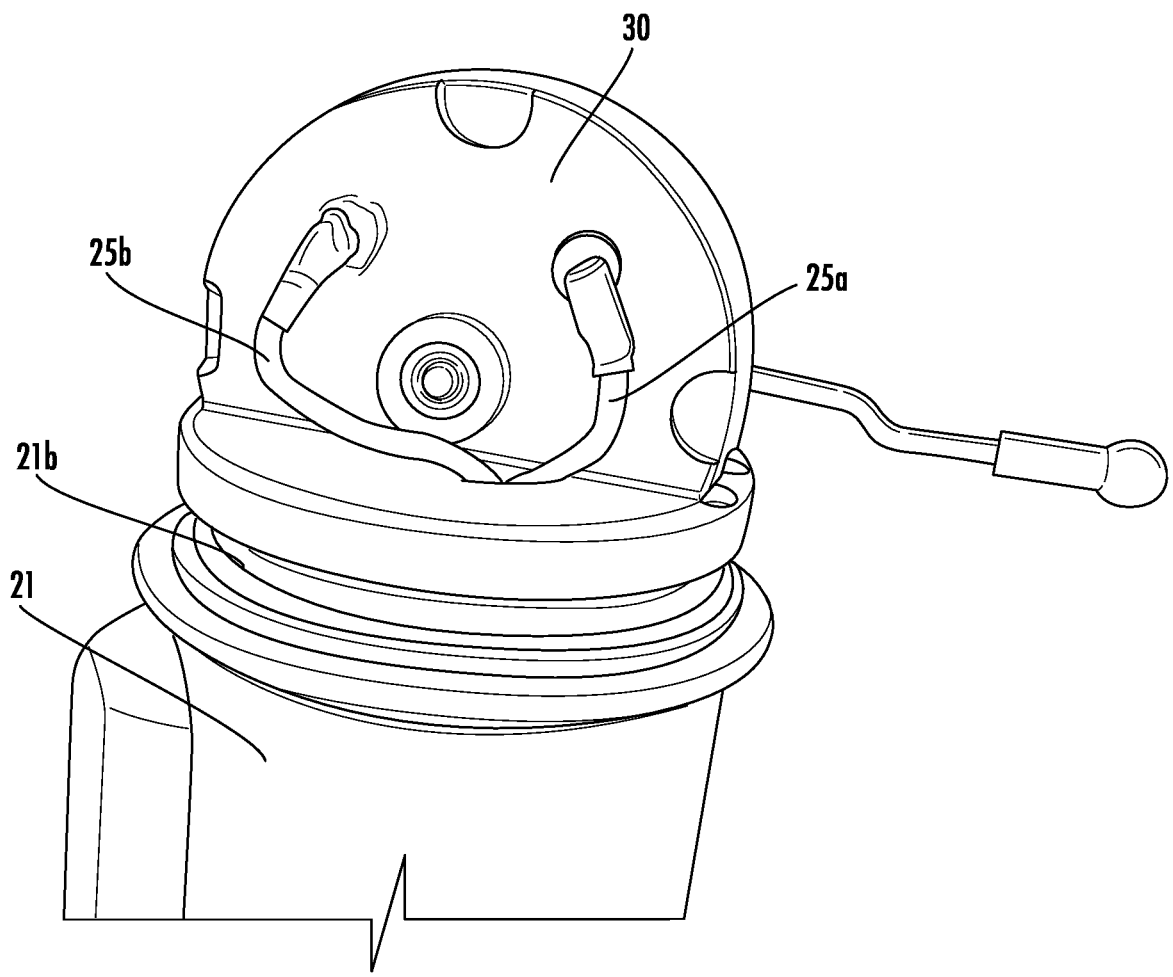
FIG. 14 is a perspective view of an end of the electronics housing connected to the motor assembly.

As shown in FIG. 14, the electronics housing 21 includes electrical connections 25a, 25b that connect to the motor assembly 30 and provide power to the motor assembly 30. The electrical connections 25a, 25b are generally defined in a middle portion of the electronics housing 21. The second end 21b of the electronics housing 21 includes a mechanical fastener, such as a screw shaft, which is separate from the electrical connections 25a, 25b, and defined along a radial rim of the electronics housing 21 to mechanically connect the electrical housing 21 to the motor housing 40.

A needle depth adjustment system 60 can be provided that adjusts the depth of a needle relative to a terminal end of the device 10. Twisting of the grip 50 relative to the needle depth adjustment system 60 varies a length of the needle extending from the device 10. One of ordinary skill in the art would understand based on the present disclosure that various forms of needle depth adjustment systems can be implemented.

Figure 10A:
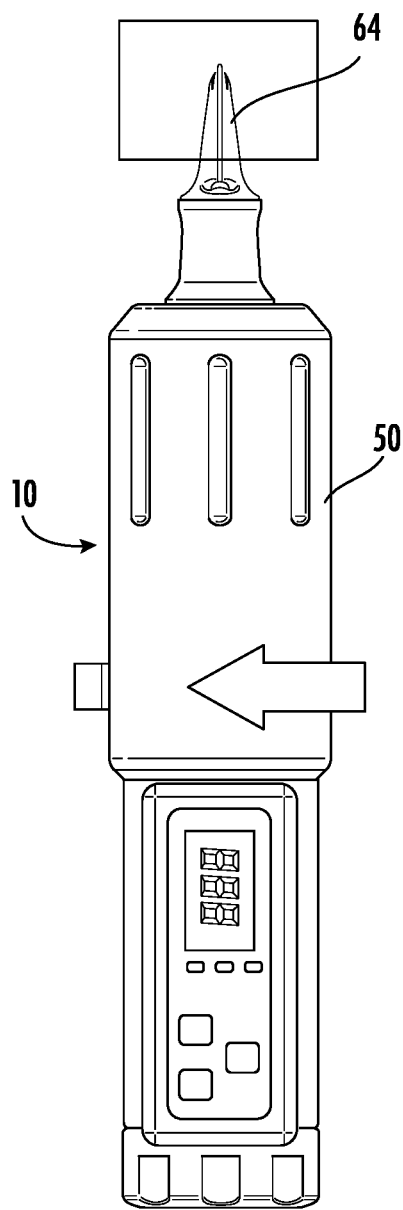
FIGS. 10A and 10B are side views of the wireless tattoo device illustrating the needle depth adjustment system.
Figure 10B:
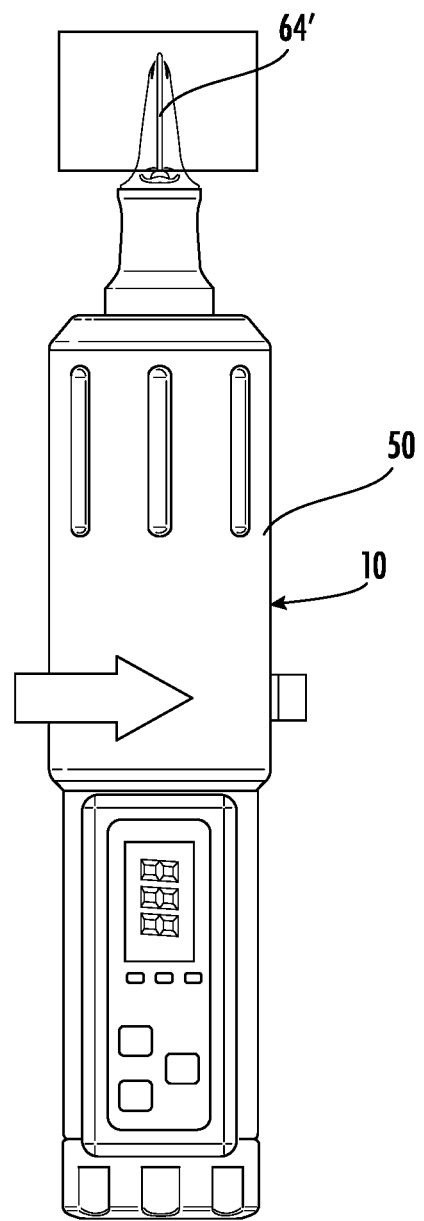

The needle depth adjustment system 60 varies a depth of a needle 64, as shown in FIGS. 10A and 10B. In FIG. 10A, the needle 64 is in an extended position. Rotation of the grip 50 relative to the needle depth adjustment system 60 then moves the needle 64 to its retracted position, shown as needle 64' in FIG. 10B.

Figure 5:
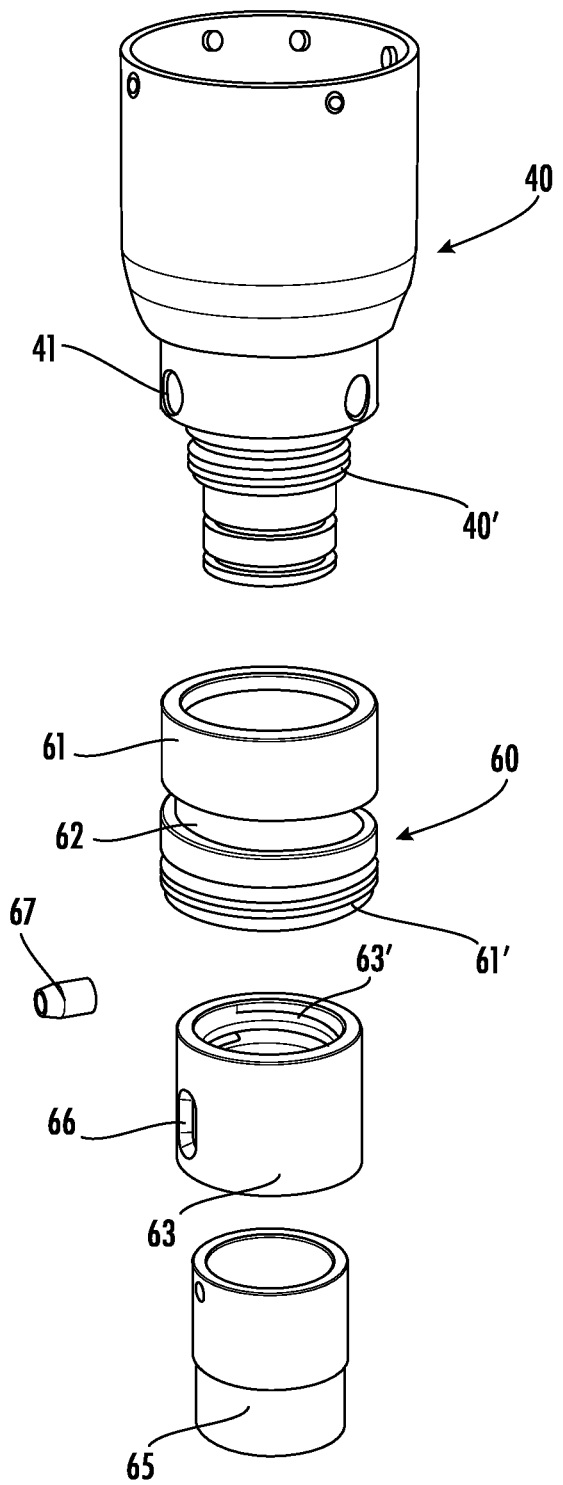
FIG. 5 is a perspective exploded view of a motor housing and needle depth adjustment system of the wireless tattoo device of FIGS. 1-3.
Figure 12C:
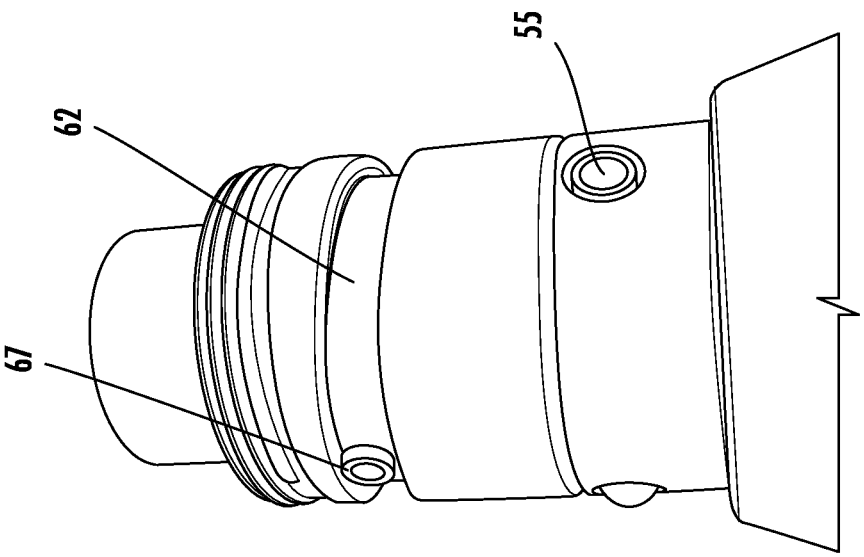
FIGS. 12A-12C illustrate further features of a depth adjustment assembly according to an embodiment.
Figure 12B:
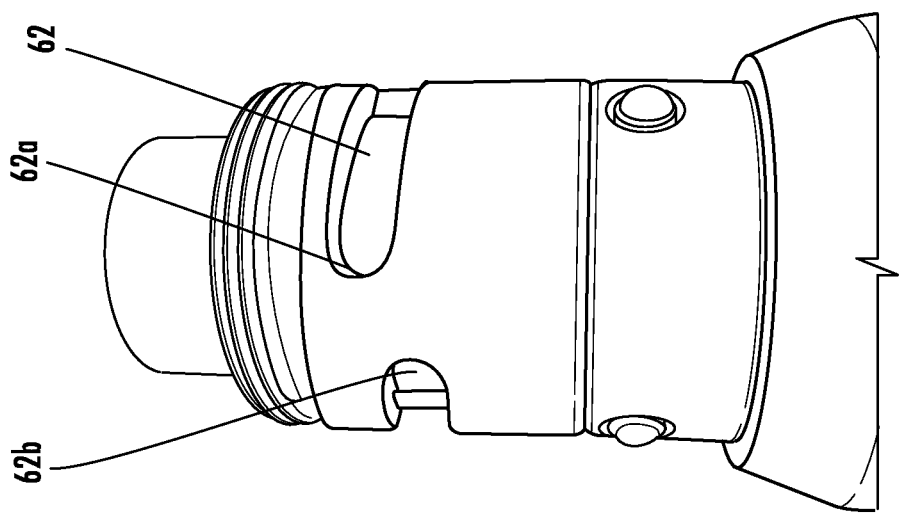
Figure 12A:
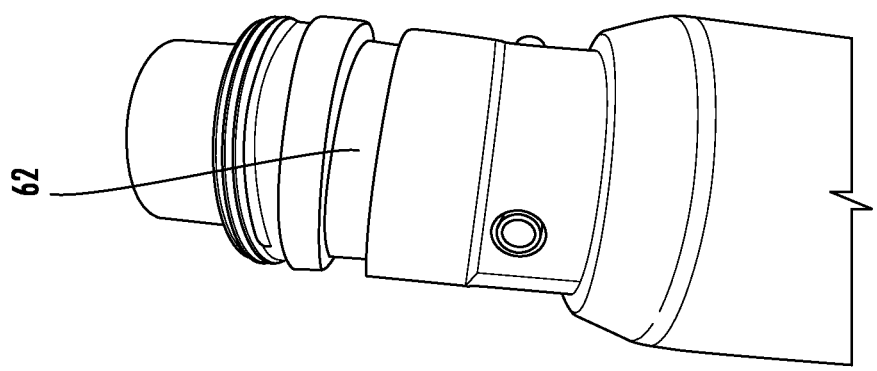

The needle depth adjustment system 60 can include a plurality of detents 55 dimensioned to frictionally engage inside of the grip 50. The detents 55 are held within recesses 41 formed on the motor housing 40. As shown in FIGS. 1 and 5, the depth adjustment system 60 includes an ink cartridge holder 65, which defines an opening dimensioned to receive the needle cartridge. A bushing 63 is also provided that includes a slot 66 for receiving a post 67 such that the post 67 is rotationally secured within the opening of the bushing 63. An adjustment housing 61 is also provided that abuts the motor housing 41 in an assembled state. The adjustment housing 61 defines a groove 62, which is also shown in FIGS. 12A-12C. In one embodiment, the groove 62 is a single revolution including ends 62a, 62b that are axially offset from each other. The offset between the groove ends 62a, 62b limits the amount of needle depth adjustment. The bushing 63 includes an internal threading 63' adapted to matingly engage with external threading 40' defined on the motor housing 40. As shown in FIG. 5, the adjustment housing 61 includes an external threading 61' that is adapted to matingly engage with internal threading defined in the grip 50. In an assembled state, the adjustment housing 61 can be rotated such that the post 67 rides along the groove 62. As the adjustment housing 61 is rotated, the needle cartridge holder 65 moves in an axial direction relative to the adjustment housing 61 to control a depth of the ink needle.

Figure 13:
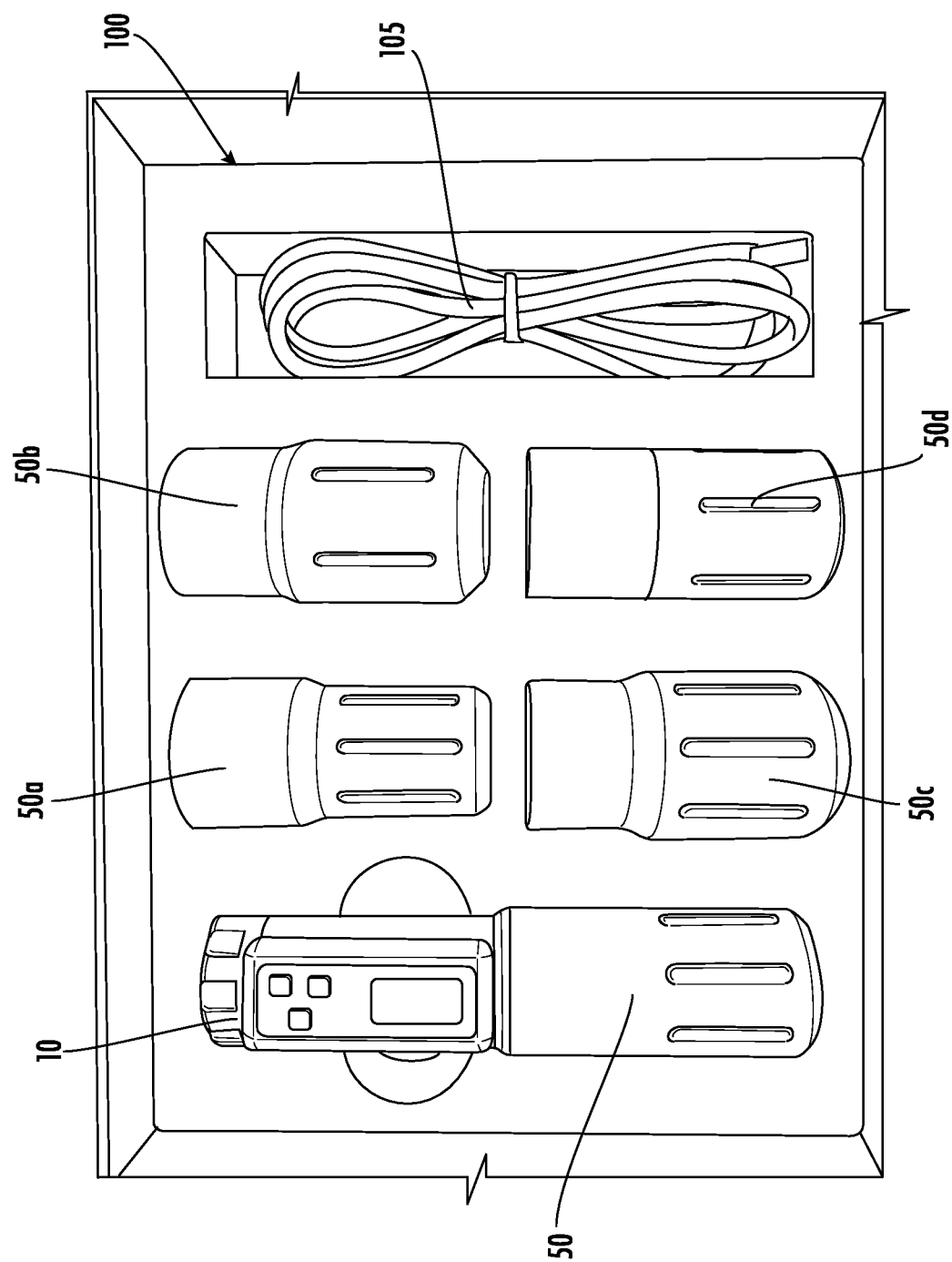
FIG. 13 is a front view of a kit including the wireless tattoo device, a plurality of grips, and a power cord.

In one embodiment, differently sized and shaped grips 50 are provided. As shown in FIG. 13, a kit 100 can be provided which includes the device 10 and a plurality of grips 50, 50a, 50b, 50c, 50d that are each adapted to mate with the motor housing 40 of the device 10. The grips 50, 50a, 50b, 50c, 50d are interchangeable and each have specific characteristics. For example, some grips 50, 50a, 50b, 50c, 50d can be formed from rubber or plastic, while other grips 50 can be formed from metal. In addition, some grips 50, 50a, 50b, 50c, 50d are intended to be disposable while others are intended to be reusable. Patterns can be included on the grips 50, 50a, 50b, 50c, 50d in order to provide a more reliable area to be held by a tattoo artist. The width of the grips 50, 50a, 50b, 50c, 50d also varies such that tattoo artists having hands of varying sizes can comfortably use the device 10. A power cord 105 is provided in the kit 100. Other components not specifically illustrated in FIG. 13 can be included in the kit 100.

The tattoo device disclosed herein has a recommended operating voltage of 5 volts to 10 volts. However, one of ordinary skill in the art would understand that the voltage can vary.

In one embodiment, the tattoo device has a stitch frequency of 40 Hz to 105 Hz. One of ordinary skill in the art would understand based on the present disclosure that the stitching frequency can vary.

The stroke is preferably 3.5 mm, +/−0.5 mm. However, the stroke can vary depending on the particular requirements.

In one embodiment, the control panel 22 includes a display with one or more indicators and/or buttons which can include, for example, an increase button 22*a*, a decrease button 22*b*, a power button 22*c*, and a display 22*d*. The control panel 22 can further include a voltage indicator 22*e*, a power indicator 22*f*, and a time indicator 22*g*. One of ordinary skill in the art would understand from the present disclosure that the control panel 22 can be modified to include different indicators and/or buttons.

In one embodiment, the control panel 22 and the power source 24 are positioned directly adjacent to each other in the electronics housing 21. This arrangement provides an axially compact configuration.

The device 10 disclosed herein includes completely modular sub-components, such as the electronics housing 21 and the motor housing 40. The electronics housing 21 and the motor housing 40 are completely detachable and re-attachable to each other.

Having thus described the present embodiments in detail, it is to be appreciated and will be apparent to those skilled in the art that many physical changes, only a few of which are exemplified in the detailed description of the disclosure, could be made without altering the inventive concepts and principles embodied therein.

It is also to be appreciated that numerous embodiments incorporating only part of the preferred embodiment are possible which do not alter, with respect to those parts, the inventive concepts and principles embodied therein.

The present embodiment and optional configurations are therefore to be considered in all respects as exemplary and/or illustrative and not restrictive, the scope of the disclosure being indicated by the appended claims rather than by the foregoing description, and all alternate embodiments and changes to this embodiment which come within the meaning and range of equivalency of said claims are therefore to be embraced therein.

What is claimed is:

1. A wireless tattoo device comprising:
    an electronics housing, a control panel, a power source, and a motor assembly driven by the power source;
    a motor housing attached to the electronics housing, the motor housing defining a passage dimensioned to receive a portion of the motor assembly, and the motor housing being configured to receive a needle cartridge, the motor housing comprising a post;
    a needle depth adjustment system comprising an adjustment housing having a portion surrounding at least a portion of the motor housing, the adjustment housing comprising a groove having a first closed end and a second closed end, the first closed end axially set off from the second closed end, the post received in the groove; and
    a grip defining an opening dimensioned to receive an end of the motor housing and the needle depth adjustment system, the motor housing and the grip being rotatable relative to each other such that a depth of the needle cartridge relative to the grip varies based on a relative rotation position between the motor housing and the grip, the grip and the adjustment housing attached wherein a rotational movement of the grip moves the post along the groove,
    wherein movement of the post within the groove is configured to adjust depth of an ink needle attached to the wireless tattoo device.

2. The device according to claim 1, wherein the electronics housing includes a power inlet.

3. The device according to claim 2, wherein the power inlet is defined on an axial end cap of the device.

4. The device according to claim 1, wherein the control panel includes an increase button, a decrease button, a power button, and a display.

5. The device according to claim 4, wherein the control panel includes a voltage indicator, a power indicator, and a time indicator.

6. The device according to claim 1, wherein the electronics housing includes an outer wall defining a window, and the window is dimensioned to receive the control panel.

7. The device according to claim 1, wherein a first end of the electronics housing is configured to engage with an end cap, and a second end of the electronics housing includes a first mating feature configured to matingly engage with a second mating feature defined on an end of the motor housing.

8. The device according to claim 1, wherein a first axial height (X1) of the electronics housing is less than a second axial height (X2) of the motor housing.

9. The device according to claim 1, wherein a first radial width (Y1) of the electronics housing is equal to or less than a second radial width (Y2) of the motor housing.

10. The device according to claim 1, wherein the motor assembly is partially housed in both the electronics housing and the motor housing.

11. The device according to claim 1, further wherein the needle depth adjustment system further comprises a needle cartridge holder configured to receive the ink needle, the needle cartridge holder configured to move in response to a rotational movement of the grip.

12. The device according to claim 1, wherein the power source is a rechargeable battery.

13. The device according to claim 1, wherein the device has an overall axial height of 131 mm, +/−10 mm, and has an outermost diameter of 32 mm, +/−5 mm.

14. The device according to claim 1, further comprising a plurality of grips, each grip of the plurality of grips having a different profile.

15. The device according to claim 1, wherein the electronics housing is completely detachable from the motor housing and re-attachable with the motor housing.

16. A kit including the device according to claim 1, wherein the kit further comprises a plurality of grips that are each adapted to mate with the motor housing of the device.

\* \* \* \* \*